United States Patent [19]

Forestier et al.

[11] Patent Number: 5,089,250
[45] Date of Patent: Feb. 18, 1992

[54] COSMETIC CONTAINING BENZOTRIAZOLE DIORGANOPOLYSILOXANES

[75] Inventors: Serge Forestier, Claye-Souilly; Gerard Lang, Saint-Gratien; Hervé Richard, Paris; Jean C. Grognet, Montlognon Senlis, all of France

[73] Assignee: L'Oreal, Paris, France

[21] Appl. No.: 479,478

[22] Filed: Feb. 13, 1990

[30] Foreign Application Priority Data

Feb. 15, 1989 [FR] France .................. 89 01990

[51] Int. Cl.$^5$ .................. A01N 25/02; A61K 7/42
[52] U.S. Cl. .................. 424/43; 424/47; 424/59; 424/60; 424/63; 424/70; 424/401; 424/DIG. 1; 424/DIG. 5; 514/844; 514/937; 514/938; 514/943; 514/943; 514/972; 528/27
[58] Field of Search .......... 424/470, 59, 60, DIG. 1, 424/DIG. 5; 514/937, 938, 943, 944; 528/27, 29

[56] References Cited

U.S. PATENT DOCUMENTS

| | | | |
|---|---|---|---|
| 4,233,430 | 11/1980 | Jacquet | 424/60 |
| 4,342,742 | 8/1982 | Sebag | 424/59 |
| 4,457,911 | 7/1984 | Conner | 424/59 |
| 4,489,057 | 12/1984 | Welters | 424/47 |
| 4,490,356 | 12/1984 | Sebag | 424/70 |
| 4,696,969 | 9/1987 | Thimineur | 524/762 |
| 4,814,162 | 3/1989 | Lang | 424/47 |
| 4,859,759 | 8/1989 | Maycock | 528/27 |
| 4,868,251 | 9/1989 | Reich | 528/27 |

FOREIGN PATENT DOCUMENTS

| | | |
|---|---|---|
| 0138321 | 4/1985 | European Pat. Off. . |
| 0354145 | 2/1990 | European Pat. Off. . |
| 2077280A | 5/1980 | United Kingdom .......... 528/27 |

*Primary Examiner*—Thurman K. Page
*Assistant Examiner*—James M. Spear
*Attorney, Agent, or Firm*—Marshall, O'Toole, Gerstein, Murray & Bicknell

[57] ABSTRACT

The cosmetic use is described, in particular for use as a UV filter, of benzotriazole diorganopolysiloxanes having either formula:

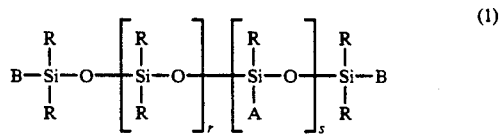

(1)

where R is $C_1$-$C_{10}$ alkyl, phenyl or 3,3,3-trifluoropropyl, B is R or A, r=0-200, s=0-50, or formulas:

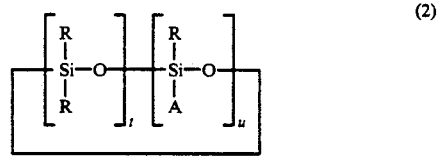

(2)

where
u=1-20, t=0-20 and t+u≧3.
A and/or B represent a benzotriazole $C_3$-$C_{12}$ alkylene which may be substituted.

13 Claims, No Drawings

COSMETIC CONTAINING BENZOTRIAZOLE DIORGANOPOLYSILOXANES

The present invention concerns the cosmetic use of benzotriazole diorganopolysiloxanes, particularly as UV filters, as well as novel cosmetic compositions containing such compounds for the protection of skin and hair.

Light of wavelengths between 280 nm and 400 nm is known to cause browning of the human epidermis; radiation of wavelengths between 280 nm and 320 nm known as UV-B causes erythema and cutaneous burns which may hinder the development of a tan; UV-B radiation must therefore be filtered out.

It is further known that UV-A radiation, with wavelengths between 320 nm and 400 nm, promotes browning of the skin and is likely to damage it, particularly with sensitive skin or where the skin is continually exposed to the sun's rays. In particular, UV-A radiation causes loss of skin elasticity and the appearance of lines resulting in premature ageing. It promotes the erythmatic reaction or amplifies it in some cases and may even be the cause of phototoxic or photallergenic reactions.

It is desirable therefore to design UV absorbing compounds so that they absorb a wide band of UV radiation in order to filter out both UV-A and UV-B.

It is further known that constituents of cosmetic preparations do not always have sufficient light stability and degrade when exposed to light.

It is thus desirable to incorporate UV filtering compounds into such preparations. These filters must also be stable and have sufficient solubility in media normally used in cosmetics, in particular oils and fats.

With hair, it is also desirable to protect it against photochemical degradation, particularly discolouring or change of shade.

Grafting molecules having a UV filtering effect onto polymer chains such as synthetic carbon polymers, natural polymers, protein hydrolysates or polyaminoamides is also known. Graft polymers as described, for example, in French patents numbers 2 197 023, 2 237 912, 2 531 960, 2 548 018, 2 549 069, 2 586 692 and 2 586 693 may be used to prepare cosmetic compositions for protection of human skin or as sun screens. However, graft polymers generally have low solubility in the usual cosmetic solvents, particularly in oily supports, and they form films having too rigid a structure.

The applicant has now discovered that, surprisingly, certain benzotriazole diorganopolysiloxanes have good cosmetic properties and good filtering properties over a wide range of wavelengths, from 280 nm to 360 nm. In particular they have excellent liposolubility and can thus be used in the fatty supports used in cosmetics. Apart from their good filtering powers and good solubility in oily media and the usual cosmetic solvents, these benzotriazole diorganopoly-siloxanes also have excellent chemical and photochemical stability and soften the skin and hair, which tolerate them well.

An object of the present invention is, then, the cosmetic use of benzotriazole diorganopolysiloxanes, particularly as UV filtering agents for radiation of wavelengths between 280 nm and 360 nm, selected from those having the formula:

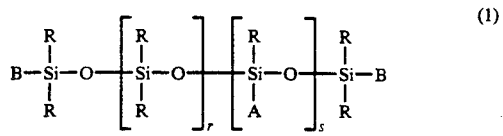

wherein:
R may be the same for each occurrence or different and is selected from $C_1$–$C_{10}$ alkyl radicals, phenyl radicals and 3,3,3-trifluoropropyl radicals, at least 80% by number of the R radicals being methyl radicals,
B may be the same for each occurrence or different and is selected from radicals R and A,
r is a number between 0 and 200 inclusive,
s is a number between 0 and 50 inclusive and if s is 0 at least one of the two B radicals is A; and from those having the formula:

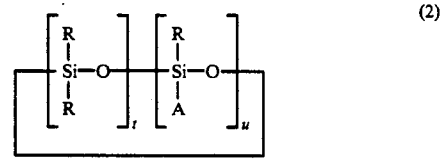

wherein:
R has the meaning defined for formula (1),
u is a number between 1 and 20 inclusive,
t is a number between 0 and 20 inclusive,
t+u is greater than or equal to 3,
and wherein in both formulae the symbol A denotes a radical having the formula:

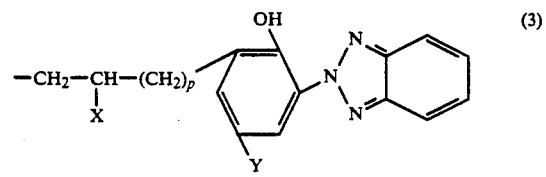

wherein:
X represents a hydrogen atom or a $C_1$–$C_4$ alkyl radical,
p is a whole number between 1 and 10,
Y represents a hydrogen atom or a $C_1$–$C_8$ alkyl radical.
In the above formulae the alkyl radicals may be linear or branched. Preferred radicals are methyl, ethyl, n-propyl, isopropyl, n-butyl, isobutyl, tertbutyl, n-amyl, isoamyl, neopentyl, n-hexyl, n-heptyl, n-octyl, 2-Ethexyl and tert-octyl.

Preferred alkyl radicals are methyl, ethyl, propyl, n-butyl, n-octyl and 2-Ethexyl.

Particularly preferred polymers are random or block polymers having formula (1) or (2) with at least one of the following features:
R is methyl,
B is methyl,
Y is methyl,
p=1,
X is a hydrogen atom or methyl radical,
r is between 5 and 20 inclusive,
s is between 2 and 15 inclusive,
t+u is between 3 and 10 inclusive.

Preparation of polymers with formula (1) and (2) may start from the corresponding polymer wherein all the A radicals are hydrogen.

This polymer is denoted by SiH; SiH groups may be present within the chain and/or at its extremities. These SiH polymers are well known in the silicone industry and are generally commercially available.

They are described, for example, in American patents U.S. Pat. Nos. 3,220,972, 3,436,366, 3,697,473 and 4,340,709.

SiH polymers may thus be selected from those having the formula:

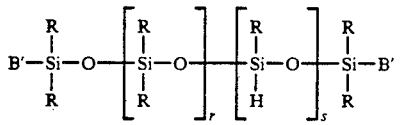
(4)

where R, r and s have the meanings given above for formula (1) and radicals B', which may be the same for each occurrence or different, are selected from radicals R and a hydrogen atom; and from those having the formula:

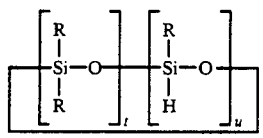
(5)

where R, t and u have the meanings given above for formula (2).

SiH polymers having formula (4) or (5) are reacted by hydrosilylation in the presence of a catalytic quantity of a platinum catalyst or an organic benzotriazole derivative selected from those having the formula:

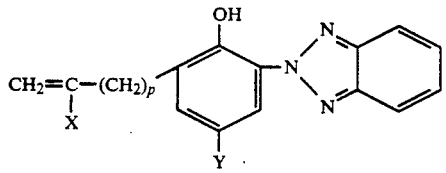
(6)

where X, Y and p have the meanings given above.

Products having formula (6) and their preparation methods are described in patent documents U.S. Pat. Nos. 4,316,033 and 4,373,060.

The recommended method is carried out in two stages. During the first stage an alkenyl halide with the formula:

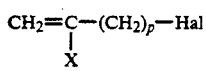
(7)

is reacted with a benzotriazole with the formula:

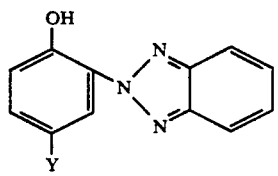
(8)

wherein X, Y and p have the meanings given above and Hal represents a halogen, preferably chlorine or bromine.

This first stage is carried out in the presence of a base, for example an alkali metal or alkaline earth hydroxide or carbonate or an alkaline amide, alcoholate or hydride, in a solvent which is compatible with the base, such as water or an organic solvent, for example an alcohol, dioxane, dimethylsulphoxide or dimethylformanide, at a temperature between room temperature and the boiling point of the solvent. A product having the following formula is obtained:

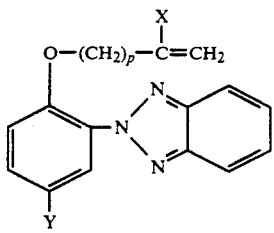
(9)

wherein X, Y and p have the meanings given above. The compound with formula (9) is then subject to a CLAISEN rearrangement to obtain the desired product with formula (6).

The CLAISEN rearrangement may be carried out under the conditions described by TARBELL (Organic Reactions, Vol. 2, John WILEY, N.Y., 1944, page 1), by heating the compound with formula (9) to at least about 170° C., if necessary in the presence of a solvent.

Platinum catalysts used for hydrosilylation of the polymers with formula (4) or (5) with the organic derivative with formula (6) are amply described in the literature. Complexes of platinum and an organic product merit particular mention. These are described in American patents U.S. Pat. Nos. 3,159,601, 3,159,602, and 3,220,972 and in European patents EP-A-57 459, EP-A-188 978 and EP-A-190 530. American patents U.S. Pat. Nos. 3,419,593, 3,377,432 and 3,814,730 describe other complexes of platinum and a vinylated organopolysiloxane.

For the reaction of the SiH polymer having formula (4) or (5) on the derivative with formula (6), the amount of platinum catalyst used comprises between 5 and 600 ppm, calculated by weight, preferably between 10 and 200 ppm based on the weight of SiH polymer having formula (4) or (5).

The hydrosilylation reaction may take place in the dry state or using a volatile organic solvent such as toluene, heptane, xylene, tetrahydrofurane or tetrachloroethylene.

It is generally desirable to heat the reaction mixture to a temperature of 60° to 120° C. for the time necessary to complete the reaction. Alternatively the SiH polymer may be added dropwise to a solution of the derivative with formula (6) in an organic solvent containing the catalyst. The SiH polymer and the derivative with formula (6) may also be added simultaneously to a suspension of the catalyst in an organic solvent.

Reaction completeness is verified by titrating residual SiH against alcoholic potash. The solvent is then eliminated, for example by distillation under reduced pressure.

The crude oil obtained can be purified, for example by passage over an absorbent silica column.

A further object of the invention is constituted by cosmetic compositions to protect the skin and hair against UV radiation, containing an effective quantity of a benzotriazole diorganopolysiloxane having formula (1) or (2), in a cosmetically acceptable medium.

A further object of the invention is a method of protecting skin and natural or sensitised hair against solar radiation, consisting in applying to the skin or hair an effective quantity of at least one compound having formula (1) or (2) in an acceptable cosmetic support comprising at least one oily phase.

"Sensitised hair" means hair which has been permed, dyed or bleached.

A still further object of the invention is a tinted or untinted, light stable cosmetic composition comprising an effective quantity of at least one benzotriazole diorganopolysiloxane having formula (1) or (2).

When used as a composition for protecting the human epidermis against ultraviolet radiation, the preparation may be in many of the diverse forms commonly used for this type of cosmetic composition. In particular, oily, alcoholic or oleoalcoholic lotions may be used, also emulsions such as creams or milks, oleoalcoholic, alcoholic or hydroalcoholic gels, solid sticks or aerosols.

It may contain any cosmetic additives normally used in this type of composition, such as thickeners, softeners, moisturisers, surfactants, preservatives, anti-foaming agents, perfumes, oils, waxes, lanolin, propellants, dyes and/or pigments to colour the composition itself or the skin, or any other ingredient normally used in cosmetics.

The compound with formula (1) or (2) is present in proportions of between 0.25 and 3% by weight with respect to the total weight of the protective cosmetic composition for the human epidermis.

An oil may be used as the solubilising solvent, or a wax or more generally any oily body, a monoalcohol or a low polyol, or a $C_{12}$-$C_{15}$ alcohol benzoate or a mixture thereof. Particularly preferred monoalcohols or polyols are ethanol, isopropanol, propyleneglycol, glycerine or sorbitol.

One embodiment of the invention is an emulsion in the form of a protective cream or milk comprising, as well as the compound with formula (1) or (2), fatty alcohols, fatty acid esters in particular fatty acid triglycerides, fatty acids, lanolin, natural or synthetic oils or waxes and emulsifiers, in the presence of water.

A further embodiment is constituted by oily lotions with bases of natural or synthetic oils or waxes, lanolin and fatty acid esters, in particular fatty acid triglycerides, or by oleoalcoholic lotions with a low alcohol base such as ethanol or a glycol such as propyleneglycol and/or a polyol such as glycerine and oils, waxes and fatty acid esters such as fatty acid triglycerides.

The cosmetic composition of the invention may also be in the form of an alcoholic gel comprising one or more alcohols or low polyols such as ethanol, propyleneglycol or glycerine and a thickener such as silica. Oleoalcoholic gels further contain a natural or synthetic oil or wax.

Solid sticks are constituted by natural or synthetic waxes and oils, fatty alcohols, fatty acid esters, lanolin and other oily substances.

For aerosol type compositions, standard propellants such as alkanes, fluoroalkanes and chlorofluoroalkanes are used.

The scope of the present invention also covers sun screening cosmetic compositions containing at least one compound with formula (1) or (2) and which may contain other UV-B and/or UV-A filters.

In this case the total quantity of filters present in the sun screen composition, i.e. the compound with formula (1) or (2) and other filters if any, lies between 0.5 and 15% by weight with respect to the total sun screen composition weight.

The forms described above for the human skin protection compositions may also be used for these sun screen compositions.

When the inventive cosmetic composition is intended to protect natural or sensitised hair from UV radiation the composition may be in the form of a shampoo, lotion, gel or rinsing emulsion, for application before or after shampooing, before or after dyeing or bleaching, before or after a perm, as a styling or treating gel, brushing or setting gel or lotion, hairspray or lacquer. As well as the inventive compound the composition may contain any of the additives used in this type of composition such as surfactants, thickeners, polymers, softeners, preservatives, foam stabilisers, electrolytes, organic solvents, siliconised derivatives, oils, waxes, degreasing agents, dyes and/or pigments to colour the composition itself or the hair or any other ingredient which is normally used in hairdressing.

It contains 0.25% to 5% by weight of the compound with formula (1) or (2).

The present invention further provides a cosmetic composition containing at least one compound with formula (1) or (2) as a protective agent against ultraviolet radiation constituted as hairdressing compositions such as hair lacquers, possibly for treating or untangling, setting lotions, tinting shampoos, hair dye compositions, cosmetic compositions such as nail polish, treatment creams and oils for the skin, foundations, lipsticks, skin care compositions such as bath oils and creams and any other cosmetic composition which may lack light stability during storage.

Such compositions contain 0.25 to 3% by weight of the compound with formula (1) or (2).

The invention further envisages a method for protecting cosmetic compositions against ultraviolet radiation consisting in incorporating an effective quantity of at least one compound with formula (1) or (2) into these compositions.

The following examples illustrate the invention without limiting its scope.

EXAMPLE 1

Preparation of a random polymer of formula:

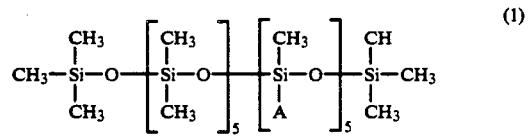

(1)

wherein A represents:

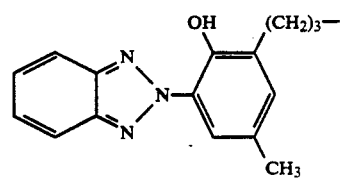

A solution of 17.1 g 3-alkyl-2-OH-5-methylphenylbenzotriazole and 10.5 g of the random polymer having the above formula where A is an atom of hydrogen was added dropwise over one hour 30 minutes to a suspension of 5% (70 mg) platinum on carbon in dry toluene (5 ml) at 90°-100° C. under nitrogen and agitation. The temperature was maintained throughout at 100° to 105° C.

The mixture was stirred and refluxed until the SiH groups had disappeared (absence of 2 180 cm$^{-1}$ infrared band), i.e. for ten hours. It was filtered over paper, the solvent eliminated and washed three times with 80% ethanol. The oil obtained was taken up in chloroform, dried over sodium sulphate and filtered over celite to eliminate the remaining colloidal platinum. After evaporation of the solvent an orange-yellow oil was obtained (weight: 26 g, yield: 95%).

UV spectrum (CHCl$_3$): $\lambda max_1$: 307 nm. $\lambda max_2$: 345 nm.

Nuclear magnetic resonance analysis ($^1$H and $^{29}$Si) indicated that the product had the desired structure.

EXAMPLE 2

18.8 g (0.071 mole) 3-alkyl-2-OH-5-methylphenylbenzotriazole, 25 ml toluene and 6 μl of a solution in hexane (8.45% by weight of platinum metal) of a platinum complex prepared from chloroplatinic acid and 1,3-divinyl-1,1,3,3-tetramethyl disiloxane as described in American patent U.S. Pat. No. 3,814,730 were placed in a 3-necked 100 ml flask held at 110° C. in an oil bath and equipped with a magnetic stirrer and a cooling coil.

Over two hours, 10 g of a random copolymer SiH having the formula:

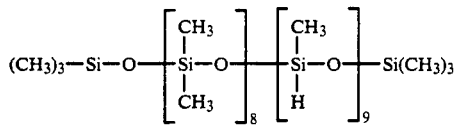

was added, which titrates 713 meq/100 g of SiH group (meq=milliequivalent).

After seven hours of reaction, titration of residual SiH against butanolic potassium indicated that 88% of SiH groups had been transformed.

A clear orange oil of very high viscosity was obtained following elimination of toluene by distillation at 110° C. under a reduced pressure of 3.3 kPa.

UV spectrum (CHCl$_3$): $\lambda max_1$: 307 nm. $\lambda max_2$: 345 nm.

Nuclear magnetic resonance analysis indicated that the product had the desired structure.

EXAMPLE 3

The same steps were carried out as in Example 2 except that the molar ratio of 3-alkyl-2-OH-5-methylphenylbenzotriazole to SiH was 1:3, i.e.

24.5 g 3-alkyl-2-OH-5-methylphenylbenzotriazole for 10 g SiH polymer.

After seven hours of reaction 90% of the SiH groups had been transformed. After elimination of toluene at 60° C. under a reduced pressure of 0.6 kPa, 32.5 g of a very viscous yellow-orange oil containing 16% by weight residual monomers was obtained.

The monomers were eliminated by passing the oil over a silica gel column (Kieselgel ART 7754, MERCK support) using, as monomer elution solvent, a 40/60 by volume dichloromethane/heptane mixture and, as oil elution solvent, ethyl acetate. After elimination of the ethyl acetate, a translucent orange gum was obtained containing 65% by weight of the desired product.

UV spectrum (CHCl$_3$): $\lambda max_1$: 307 nm. $\lambda max_2$: 345 nm.

EXAMPLES OF USE

Example A

Oil-in-Water Sun Screen Emulsion

| | |
|---|---|
| Compound from example 1 | 3.0 g |
| oxyethylenated cetylstearyl alcohol (C$_{16}$/C$_{18}$-35 65) (150E) ("MERGITAL CS15" from HENKEL) | 3.0 g |
| Glycerol monostearate | 4.8 g |
| Myristic alcohol | 4.5 g |
| Benzoate of alcohols C12/C15 ("FINSOLV TN" from WITCO) | 18.0 g |
| Propylene glycol | 6.0 g |
| Preservative | 0.2 g |
| Perfume | 0.6 g |
| Demineralised water        qsp | 100 g |

The oily substances and emulsifiers were heated to 80°-85° C. and the compound of Example 1 added. Alternatively, the water containing the hydrosoluble compounds may be heated to 80°-85° C. and the oily phase added to the aqueous phase. After ten minutes of brisk stirring, the mixture was allowed to cool under moderate stirring, then the perfume and preservative was added.

Example B:

Sun Screen Stick

| | |
|---|---|
| Compound from example 1 | 3.0 g |
| Hydrocarbonated mineral wax | 20.0 g |
| Beeswax | 7.0 g |
| Oleic alcohol | 12.0 g |
| Hydrogenated lanolin | 8.0 g |
| Liquid lanolin | 8.0 g |
| Carnauba wax | 1.0 g |
| Benzoate of alcohols C$_{12}$/C$_{15}$ ("FINSOLV TN" from WITCO) | 20.0 g |
| Perfume | 1.2 g |
| Vaseline        qsp | 100 g |

Example C

Oil-in-Water Emulsion for Protection of the Human Epidermis

| | |
|---|---|
| Compound from example 2 | 2 g |
| Oxyethylenated cetylstearyl alcohol, 15 moles O.E. | 3 g |
| Glycerol monostearate | 4.8 g |
| Myristic alcohol | 4.5 g |
| Benzoate of alcohols C$_{12}$/C$_{15}$ | 18.0 g |
| Propylene glycol | 6.0 g |
| Preservative | 0.2 g |
| Perfume | 0.6 g |
| Demineralised water        qsp | 100 g |

This emulsion was prepared as in Example 1.

Example D

Sun Screen Stick

| | |
|---|---|
| Compound from example 3 | 2 g |
| Compound from example 2 | 1 g |

| | |
|---|---|
| Hydrocarbonated mineral wax | 20 g |
| Beeswax | 7 g |
| Oleic alcohol | 12 g |
| Hydrogenated lanolin | 8 g |
| Liquid lanolin | 8 g |
| Carnauba wax | 1 g |
| Benzoate of alcohols $C_{12}/C_{15}$ | 20 g |
| Perfume | qs |
| Vaseline | qsp 100 g |

Example E

Sun Screen Cream

| | |
|---|---|
| Compound from example 3 | 5 g |
| Mixture of cetylstearyl alcohol and oxyethylenated cetylstearyl alcohol, 33 moles ethylene oxide ("SINNOWAX 10" from HENKEL) | 7 g |
| Mixture of glycerol mono and distearate, non-autoemulsionable | 2 g |
| Cetyl alcohol | 1.5 g |
| Benzoate of $C_{12}/C_{15}$ alcohols ("FINSOLV TN" from WITCO) | 15 g |
| Polydimethylsiloxane | 1.5 g |
| Glycerine | 20 g |
| Perfume, preservative | qs |
| Perfume, preservative | qsp 100 g |

This cream was prepared by following the standard emulsion preparation technique of dissolving the filter in the oily phase containing the emulsionates, heating the oily phase to 70°-80° C. and adding, under brisk agitation, the water heated to the same temperature. Agitation was maintained for 10 to 15 minutes then the mixture was allowed to cool under moderate agitation and at a temperature of about 40° C. the perfume and preservative were added.

The above examples A to E illustrate compositions for application to the skin to protect it against UV radiation.

The following examples are illustrations of compositions for the hair.

Example F

Hair Protection Lotion

| | |
|---|---|
| Compound from example 1 | 1.4 g |
| Benzoate of $C_{12}/C_{15}$ alcohols ("FINSOLV TN" from WITCO) | qsp 100 g |

This clear solution applied to wet hair makes the dried hair shiny, soft and voluminous whilst protecting it from the sun.

Example G

Hair Protection Lotion

| | |
|---|---|
| Compound from example 2 | 5 g |
| Absolute ethanol | 10 g |
| $C_8$-$C_{12}$ fatty acid triglycerides ("MIGLYCOL 812" from DYNAMIT NOBEL) | qsp 100 g |

This lotion is a slightly amber, clear liquid.

When applied to washed and rinsed, wet hair this lotion facilitates styling and protects the dried hair from ultraviolet radiation.

We claim:

1. A cosmetic composition which comprises at least one cosmetically acceptable solvent, at least one cosmetic additive selected from thickeners, softeners, moisturizers, surfactants, preservatives, anti-foaming agents, perfumes, oils, waxes, lanolin, propellants, dyes and pigments, and an effective quantity for protecting the skin and hair against UV radiation in the range of 280 to 360 nm wavelengths of at least one benzotriazole diorganopolysiloxane having the formula:

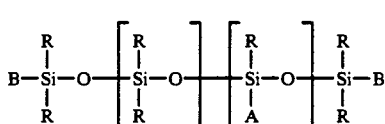

(1)

wherein:
R may be the same for each occurrence or different and is selected from $C_1$-$C_{10}$ alkyl radicals, phenyl radicals and 3,3,3-trifluoropropyl radicals, at least 80% by number of the R radicals being methyl radicals,
B may be the same for each occurrence or different and is selected from radicals R and A,
r is a number between 0 and 200 inclusive,
s is a number between 0 and 50 inclusive and if s is 0 at least one of the two B radicals is A;
or the formula:

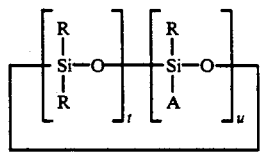

(2)

wherein:
R has the meaning defined for formula (1),
u is a number between 1 and 20 inclusive,
t is a number between 0 and 20 inclusive,
t+u is greater than or equal to 3;
and wherein in both formulae the symbol A denotes a radical having the formula:

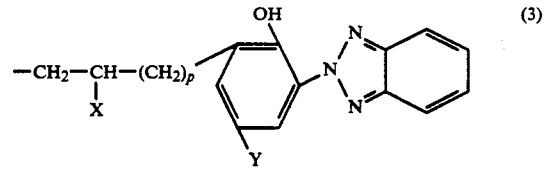

(3)

wherein:
X represents a hydrogen atom or a $C_1$-$C_4$ alkyl radical,
p represents a whole number between 1 and 10, and
Y represents a hydrogen atom or a $C_1$-$C_8$ alkyl radical.

2. A cosmetic composition according to claim 1 which comprises a random or block benzotriazole diorganopolysiloxane having at least one of the following features: R is methyl, B is methyl, r is between 5 and 20 inclusive, s is between 2 and 15 inclusive, t+u is between 3 and 10 inclusive, X is H or methyl, p=1 and Y is methyl.

3. A cosmetic composition according to claim 1 which comprises a polydimethylsiloxane grafted with 3-alkyl-2-OH-5-methylphenylbenzotriazole having formula (1) wherein R and B represent a methyl group, r=5, s=5.

4. A cosmetic composition according to claim 1 which comprises a polydimethylsiloxane grafted with 3-alkyl-2-OH-5-methylphenylbenzotriazole having formula (1) wherein R and B represent a methyl group, r=8, and s=9.

5. A cosmetic composition according to claim 1 which additionally contains a cosmetically acceptable solvent selected from water, oils, waxes, low monoalcohols and polyols, $C_{12}$-$C_{15}$ alcohol benzoates, and mixtures thereof.

6. A cosmetic composition according to claim 1 which is in the form of an oily, alcoholic or oleoalcoholic lotion, emulsion, oleoalcoholic, alcoholic or hydroalcoholic gel, solid stick, spray or aerosol.

7. A cosmetic composition according to claim 1 which constitutes a protective composition for the human skin and contains 0.25 to 3% by weight of diorganopolysiloxane having formula (1) or (2).

8. A cosmetic composition according to claim 1 in the form of a sun screen which contains 0.5 to 15% by weight of diorganopolysiloxane having formula (1) or (2).

9. A sun screening cosmetic composition according to claim 8 which further contains a filtering agent for UV-B and/or UV-A radiation.

10. A cosmetic composition according to claim 1 for application to the hair which is in the form of a shampoo, lotion, rinsing gel or emulsion, for application before or after shampooing, before or after dyeing or bleaching, before or after a perm, as a styling or treatment lotion or gel, a brushing or setting lotion or gel, hair spray or hair lacquer and, comprises 0.25 to 5% by weight of diorganopolysiloxane having formula (1) or (2).

11. A cosmetic composition according to claim 1 in the form of coloured or non-coloured cosmetic composition which is the form of a hairdressing composition, a cosmetic or a product for caring or treating the skin, comprising 0.25 to 3% by weight of diorganopolysiloxane having formula (1) or (2).

12. A process for the cosmetic treatment of the skin or the hair which consists in applying to the skin or the hair
    a cosmetic composition containing an effective amount to provide protection against UV radiation in the range of 280 to 360 nm wavelengths of a benzotriazole diorganopolysiloxane having the formula:

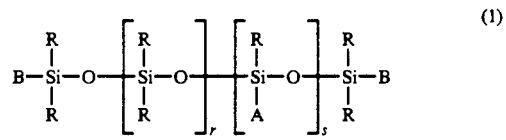

(1)

wherein:
R may be the same for each occurrence or different and is selected from $C_1$-$C_{10}$ alkyl radicals, phenyl radicals and 3,3,3-trifluoropropyl radicals, at least 80% by number of the R radicals being methyl radicals,
B may be the same for each occurrence or different and is selected from radicals R and A,
r is a number between 0 and 200 inclusive,
s is a number between 0 and 50 inclusive, and if s is 0, at least one of the two B radicals is A;
or having the formula:

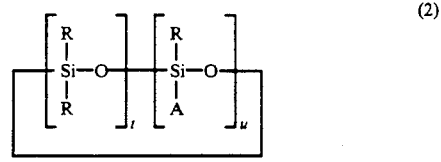

(2)

wherein:
R has the meaning defined for formula (1),
u is a number between 1 and 20 inclusive,
t is a number between 0 and 20 inclusive,
t+u is greater than or equal to 3;
and wherein both formulae the symbol A denotes a radical having the formula:

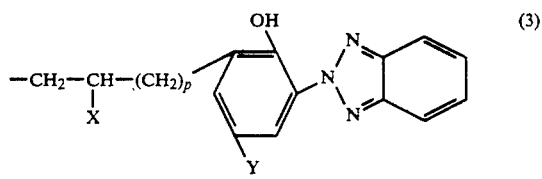

(3)

wherein:
X represents a hydrogen atom or a $C_1$-$C_4$ alkyl radical,
p represents a whole number between 1 and 10,
Y represents a hydrogen atom or a $C_1$-$C_8$ alkyl radical.

13. A method of protecting a cosmetic composition against ultraviolet radiation which consists in incorporating into said composition an effective quantity to provide UV protection in the range of 280 to 360 nm wavelengths of a benzotriazole diorganopolysiloxane having the formula:

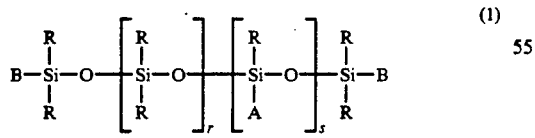

(1)

wherein:
R may be the same for each occurrence or different and is selected from $C_1$-$C_{10}$ radicals, phenyl radicals and 3,3,3-trifluoropropyl radicals, at least 80% by number of the R radicals being methyl radicals,
B may be the same for each occurrence or different and is selected from radicals R and A,
r is a number between 0 and 200 inclusive,
s is a number between 0 and 50 inclusive, and if s is 0, at least one of the two B radicals is A;
or having the formula:

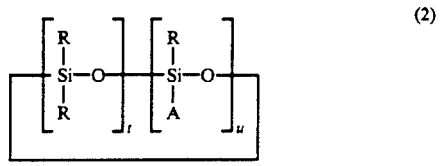

(2)

wherein:

R has the meaning defined for formula (1), u is a number between 1 and 20 inclusive, t is a number between 0 and 20 inclusive, t+u is greater than or equal to 3;

and wherein both formulae the symbol A denotes a radical having the formula:

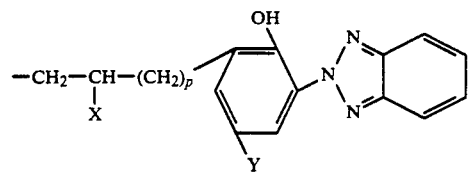

wherein:
X represents a hydrogen atom or a $C_1$-$C_4$ alkyl radical,
p represents a whole number between 1 and 10,
Y represents a hydrogen atom or a $C_1$-$C_8$ alkyl radical.

* * * * *